United States Patent
Ryu et al.

(10) Patent No.: US 10,779,797 B2
(45) Date of Patent: Sep. 22, 2020

(54) ULTRASONIC DIAGNOSTIC SYSTEM AND DIAGNOSTIC METHOD APPLICABLE TO WIRELESS COMMUNICATION TERMINAL HAVING VARIOUS RESOLUTION LEVELS

(71) Applicant: HEALCERION CO., LTD., Seoul (KR)

(72) Inventors: Jeong Won Ryu, Seoul (KR); You Chan Choung, Seoul (KR); Wook Jin Chung, Seoul (KR)

(73) Assignee: HEALCERION CO., LTD., Seoul (KR)

( * ) Notice: Subject to any disclaimer, the term of this patent is extended or adjusted under 35 U.S.C. 154(b) by 1014 days.

(21) Appl. No.: 15/304,213

(22) PCT Filed: Mar. 13, 2015

(86) PCT No.: PCT/KR2015/002433
§ 371 (c)(1),
(2) Date: Oct. 14, 2016

(87) PCT Pub. No.: WO2015/167122
PCT Pub. Date: Nov. 5, 2015

(65) Prior Publication Data
US 2017/0035390 A1    Feb. 9, 2017

(30) Foreign Application Priority Data
Apr. 28, 2014   (KR) .................. 10-2014-0050669

(51) Int. Cl.
| A61B 8/00 | (2006.01) |
| G01N 29/24 | (2006.01) |
| A61B 8/14 | (2006.01) |
| A61B 8/08 | (2006.01) |

(52) U.S. Cl.
CPC .............. *A61B 8/4472* (2013.01); *A61B 8/00* (2013.01); *A61B 8/14* (2013.01); *A61B 8/4411* (2013.01); *A61B 8/4427* (2013.01); *A61B 8/461* (2013.01); *A61B 8/464* (2013.01); *A61B 8/5207* (2013.01); *A61B 8/54* (2013.01); *A61B 8/56* (2013.01); *A61B 8/565* (2013.01); *G01N 29/24* (2013.01);

(Continued)

(58) Field of Classification Search
None
See application file for complete search history.

(56) References Cited

U.S. PATENT DOCUMENTS

2010/0331689 A1* 12/2010 Wegener .................. A61B 8/06
                                                                            600/443
2014/0064025 A1*  3/2014 Nakamichi ............... G01S 7/58
                                                                            367/11

* cited by examiner

*Primary Examiner* — Joel F Brutus
(74) *Attorney, Agent, or Firm* — Harness, Dickey & Pierce, P.L.C.

(57) ABSTRACT

The present disclosure provides an ultrasonic diagnostic system formed of an ultrasonic diagnostic apparatus and a wireless communication terminal and applicable to a wireless communication terminal with various resolution levels, including the ultrasonic diagnostic apparatus which converts frame data obtained by collecting an echo signal at an ultrasonic probe into scan data corresponding to a resolution level of a display screen of the wireless communication terminal and the wireless communication terminal which receives the scan data from the ultrasonic diagnostic apparatus and scan-converts the scan data into an ultrasonic image adequate for the resolution level of the display screen thereof.

5 Claims, 5 Drawing Sheets

(52) U.S. Cl.
CPC ........ *G01N 29/2481* (2013.01); *A61B 8/4433* (2013.01)

(PRIOR ART)

ULTRASONIC DIAGNOSTIC SYSTEM AND DIAGNOSTIC METHOD APPLICABLE TO WIRELESS COMMUNICATION TERMINAL HAVING VARIOUS RESOLUTION LEVELS

CROSS-REFERENCE TO RELATED APPLICATIONS

This application is a national phase application of PCT Application No. PCT/KR2015/002433, filed on 13 Mar. 2015, which claims benefit of Korean Patent Application 10-2014-0050669, filed on 28 Apr. 2014. The entire disclosure of the applications identified in this paragraph are incorporated herein by reference.

FIELD

The present invention relates to an ultrasonic diagnostic system and method applicable to a wireless communication terminal with various resolution levels, and more particularly, to an ultrasonic diagnostic system and method applicable to a wireless communication terminal with various resolution levels, capable of embodying resolution adequate for the wireless communication terminal with various resolution levels and efficiently utilizing a transmission/reception bandwidth at the same time.

BACKGROUND

With noninvasive and nondestructive properties, ultrasonic diagnostic apparatuses are generally used in the medical field to obtain information of the inside of an object. Since it is possible to provide a high-resolution image of internal organizations of the object to a doctor with no surgical operations of directly incising and observing the object, ultrasonic diagnostic systems are very importantly used in the medical field.

Ultrasonic diagnostic apparatuses are systems which emit an ultrasonic signal from a body surface of an object toward a target portion inside the object, extract information from a reflected ultrasonic signal, and obtain an image of a section of soft tissue or a blood flow in a noninvasive manner.

Compared with other imaging diagnostic apparatuses such as X-ray inspection apparatuses, computerized tomography (CT) scanners, magnetic resonance image (MRI) scanners, and nuclear medicine inspection apparatuses, since having a small size, being cheap, being capable of displaying in real time, and having excellent safety without being exposed to X-rays, ultrasonic diagnostic systems described above are generally used to diagnose hearts, internal organs in an abdominal cavity, urinary systems, and genital organs.

FIG. 1 is a block diagram schematically illustrating an ultrasonic diagnostic system.

As shown in the drawing, the ultrasonic diagnostic system includes an ultrasonic probe 10, a beam former 20, a scan-converting portion 30, and a display portion 40.

The ultrasonic probe 10 transmits an ultrasonic signal to an object and forms a reception signal by receiving an echo signal reflected from the object. Also, the ultrasonic probe 10 includes at least one transducer element which operates to transduce an ultrasonic signal and an electric signal into each other.

The beam former 20 analog/digital-converts and time-delays the reception signal provided from the ultrasonic probe 10 considering a position and a focused point of each of the transducer elements and forms frame data by adding up time-delayed digital signals.

The scan-converting portion 30 generates an ultrasonic image by performing scan-conversion to display the frame data on a display screen of a display portion.

The display portion 40 displays scan-converted ultrasonic data as the ultrasonic image on the display screen.

FIG. 2 is a view of a conventional ultrasonic diagnostic system used in a clinic.

As shown in the drawing, since the conventional ultrasonic diagnostic system has a monitor for displaying to display an ultrasonic image which is fixedly mounted therein, the ultrasonic image is generated according to a certain resolution level.

Recently, it has been tried to perform ultrasonic diagnosis by connecting various wireless communication terminals such as a smart phone and a tablet personal computer to the ultrasonic diagnostic system through wireless communication.

However, since wireless communication terminals described above include a display with various resolution levels, it is necessary to adjust a resolution level to transmit an ultrasonic image with a resolution level different from that of a general ultrasonic diagnostic system to a wireless communication terminal.

In addition, when the wireless communication terminal includes a display portion with a resolution level lower than an ultrasonic image generated by the ultrasonic diagnostic system, it is impossible to efficiently utilize a transmission/reception bandwidth when the ultrasonic image generated by the general ultrasonic diagnostic system is transmitted to the wireless communication terminal.

Accordingly, a practical and applicable technology with respect to an ultrasonic diagnostic system capable of providing resolution adequate for a wireless communication terminal with various resolution levels and efficiently utilizing a transmission/reception bandwidth at the same time is urgently needed.

DISCLOSURE

Technical Problem

The present invention provides an ultrasonic diagnostic system and method capable of providing resolution adequate for a wireless communication terminal with various resolution levels and efficiently utilizing a transmission/reception bandwidth at the same time.

Technical Solution

One aspect of the present invention provides an ultrasonic diagnostic system formed of an ultrasonic diagnostic apparatus and a wireless communication terminal and applicable to a wireless communication terminal with various resolution levels, including the ultrasonic diagnostic apparatus which converts frame data obtained by collecting an echo signal at an ultrasonic probe into scan data corresponding to a resolution level of a display screen of the wireless communication terminal and the wireless communication terminal which receives the scan data from the ultrasonic diagnostic apparatus and scan-converts the scan data into an ultrasonic image adequate for the resolution level of the display screen thereof.

The ultrasonic diagnostic apparatus may include an ultrasonic probe which transmits an ultrasonic signal to an object and receives an echo signal reflected by the object, a beam former which generates frame data by collecting the echo signal reflected from the ultrasonic probe, a resolution information reception portion which receives resolution information from the wireless communication terminal, a scan data resolution database (DB) in which scan data capable of corresponding to the resolution information of the wireless communication terminal with various resolution levels and increasing efficiency of a bandwidth while performing wireless communication, a scan data generation portion which compares the resolution information received by the resolution information reception portion with mapping information of the scan data resolution DB and generates scan data to be transmitted to the wireless communication terminal using the frame data, and a scan data transmission portion which transmits the scan data generated by the scan data generation portion to the wireless communication terminal.

The wireless communication terminal may include a display portion which displays an ultrasonic image, a resolution information generation portion which generates resolution information corresponding to a display screen of the display portion, a data transmission/reception portion which transmits and receives the resolution information and scan data by performing wireless communication with the ultrasonic diagnostic apparatus, a scan-conversion resolution DB in which a size of an ultrasonic image capable of being scan-converted corresponding to the resolution information, which is set and mapped in advance, is stored, an application control portion which maps an ultrasonic image corresponding to the resolution information of the display screen using the scan-conversion resolution DB, and a scan-conversion portion which scan-converts the scan data received from the ultrasonic diagnostic apparatus into an ultrasonic image adequate for a resolution level of the display screen.

Another aspect of the present invention provides a diagnostic method of an ultrasonic diagnostic system applicable to a wireless communication terminal with various resolution levels and including an ultrasonic diagnostic apparatus which forms scan data corresponding to a resolution level of a display screen of the wireless communication terminal using frame data obtained by collecting an echo signal from an ultrasonic probe and the wireless communication terminal which receives the scan data from the ultrasonic diagnostic apparatus and scan-convert the scan data into an ultrasonic image adequate for the resolution level of the display screen. The method includes a first operation of generating the frame data, by a beam former, by collecting the echo signal of the ultrasonic probe, a second operation of generating resolution information of the display screen, by a resolution generation portion of the wireless communication terminal, using a device driver, a third operation of transmitting the resolution information from the wireless communication terminal to the ultrasonic diagnostic apparatus through a data transmission/reception portion of the wireless communication terminal and a resolution information reception portion of the ultrasonic diagnostic apparatus, a fourth operation of comparing the resolution information of the wireless communication terminal with mapping information of a scan data resolution DB and then generating scan data to be transmitted to the wireless communication terminal using the frame data generated by the beam former according to the mapping information, a fifth operation of transmitting the scan data from the ultrasonic diagnostic apparatus to the wireless communication terminal through a scan data transmission portion of the ultrasonic diagnostic apparatus and the data transmission/reception of the wireless communication terminal, a sixth operation of mapping an ultrasonic image corresponding to the resolution information, by an application control portion, by referring to a scan-conversion resolution DB and then scan-converting the scan data received from the ultrasonic diagnostic apparatus, by a scan-conversion portion, into an ultrasonic image adequate for the resolution information of the display screen, and a seventh operation of displaying the ultrasonic image on which scan conversion is completed by a display portion.

Advantageous Effects

As described above, according to the embodiments of the present invention, since frame data formed by a beam former of an ultrasonic diagnostic apparatus is formed as scan data corresponding to a resolution level of a wireless communication terminal and then transmitted to the wireless communication terminal, a transmission/reception bandwidth may be efficiently utilized.

Also, since the scan data transmitted from the ultrasonic diagnostic apparatus may be independently scan-converted into an adequate resolution level, there are provided an ultrasonic diagnostic system and method applicable to a wireless communication terminal with various resolution levels.

MODE FOR INVENTION

Embodiments of the present invention are provided to more completely explain the present invention to one of ordinary skill in the art and following embodiments may be modified into various other forms and the scope of the present invention is not limited thereto. The embodiments are provided to make the disclosure full and complete and to completely convey the concept to those skilled in the art.

The terms are used herein only to explain particular embodiments but do not limit the present invention. As used herein, singular expressions, unless contextually defined otherwise, may include plural expressions. Also, the terms "comprise" and/or "comprising" are used herein to specify the present of stated forms, numbers, steps, operations, members, elements, and/or groups thereof but don not preclude the presence or addition of one or more other forms, numbers, operations, members, elements and/or groups thereof. As used herein, the term "and/or" includes any and all combinations or one of a plurality of associated listed items.

It should be understood that although the terms "first", "second", etc. are used herein to describe various members, areas, layers, and/or portions, these members, areas, layers and/or portions are not limited by these terms. These terms do not mean particular order, top and bottom, or ratings but are used only to distinguish one member, area, or portion from another member, area, or portion. Accordingly, a first member, area, or portion which will be described below may be referred to as a second member, area, or portion without departing from the scope of the present invention.

Hereinafter, exemplary embodiments of the present invention will be described in detail with reference to the attached drawings.

Figure 1:
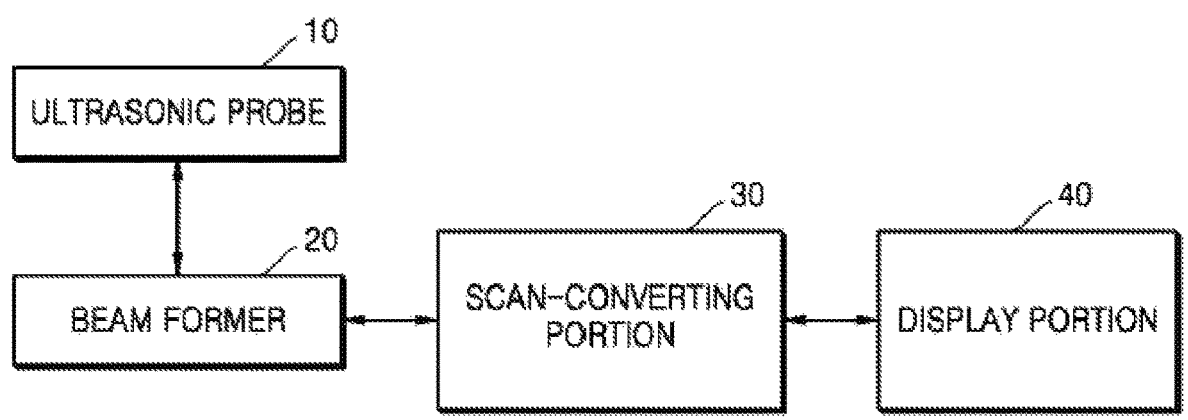
FIG. 1 is a block diagram schematically illustrating a conventional ultrasonic diagnostic system.
Figure 2:
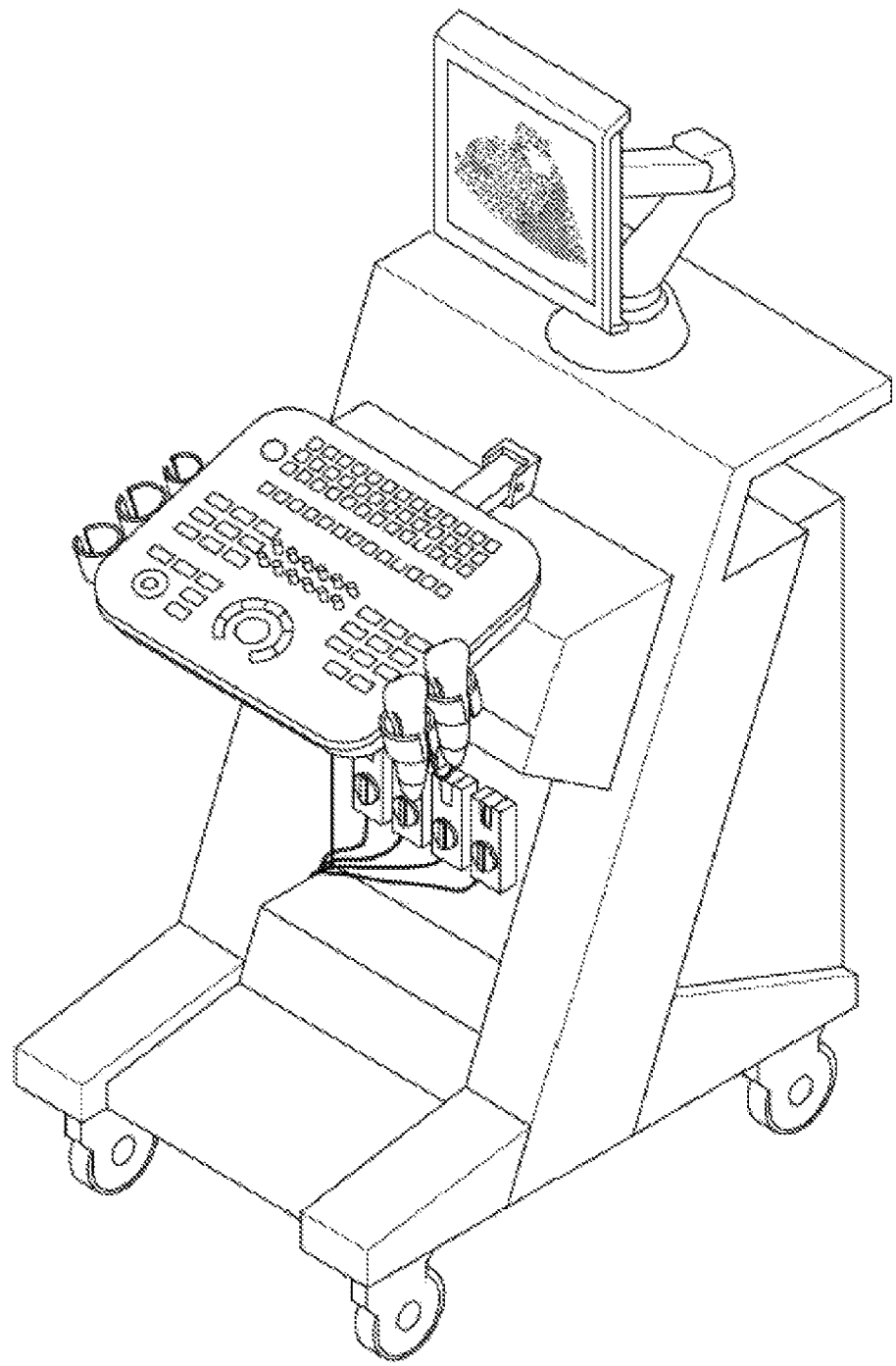
FIG. 2 is a view of a conventional ultrasonic diagnostic system used in a clinic.
Figure 3:
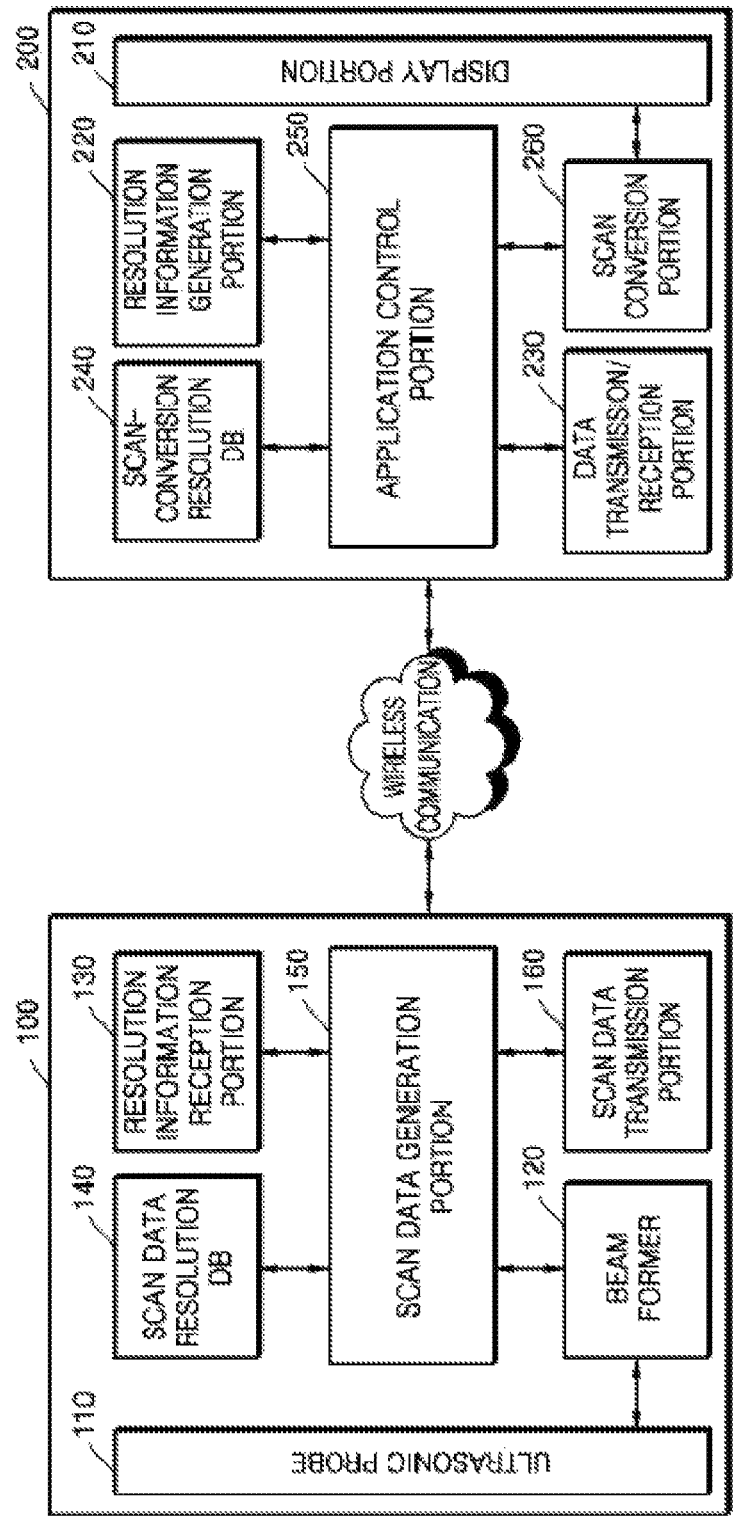
FIG. 3 is a block diagram of an ultrasonic diagnostic system applicable to a wireless communication terminal with various resolution levels according to an embodiment of the present invention.

FIG. 3 is a block diagram of an ultrasonic diagnostic system applicable to a wireless communication terminal with various resolution levels according to an embodiment of the present invention.

As shown in the drawings, the ultrasonic diagnostic system applicable to a wireless communication terminal with various resolution levels according to the embodiment of the present invention includes an ultrasonic diagnostic apparatus 100 and a wireless communication terminal 200 which transmit and receive ultrasonic image signals through wireless communication.

The ultrasonic diagnostic apparatus 100 may form scan data using frame data obtained from an ultrasonic probe 110 to correspond to a resolution level of a display screen of the wireless communication terminal 200 and to have an optimal bandwidth adequate for data transmission.

Also, the wireless communication terminal 200 may receive the scan data from the ultrasonic diagnostic apparatus 100 and may scan-convert the scan data into an ultrasonic image adequate for a resolution level of its own display.

In more detail, the ultrasonic diagnostic apparatus 100 may include the ultrasonic probe 110, a beam former 120, a resolution information reception portion 130, a scan data resolution database (DB) 140, a scan data generation portion 150, and a scan data transmission portion 160.

The ultrasonic probe 110 may transmit an ultrasonic signal to an object and may receive an echo signal reflected from the object.

Also, the beam former 120 may collect the echo signal reflected from the ultrasonic probe 110 and may generate frame data.

The resolution information reception portion 130 may receive resolution information from the wireless communication terminal 200.

Following Table 1 shows a type of a wireless communication terminal with various resolution levels.

TABLE 1

| Operating system | Resolution | Product names |
|---|---|---|
| IOS | 320 × 480 | iPhone 3 |
| | 640 × 960 | iPhone 4 |
| | 640 × 1136 | iPHone 5 |
| | 768 × 1024 | iPad 1, iPad 2, iPad mini |
| | 1536 × 2048 | iPad 3, iPad 4 |
| Android | 480 × 800 | Galaxy S, Galaxy S2, Nexus S, HTC desired Hd |
| | 800 × 1280 | Galaxy Tab 10.1, Galaxy Note 1, Nexus 7 |
| | 720 × 1280 | Galaxy S3, Galaxy S2 HD, |

TABLE 1-continued

| Operating system | Resolution | Product names |
|---|---|---|
| | | Galaxy Note 2, Optimus G |
| | 1200 × 1920 | Nexus 7 (2013) |
| | 1080 × 1920 | G2, Galaxy S4, Galaxy Note 3 |

As shown in Table 1, a wireless communication terminal applicable to the embodiment of the present invention may have various resolution levels.

Accordingly, when the ultrasonic diagnostic apparatus 100 transmits an ultrasonic image to the wireless communication terminal 200, to prevent a distortion of an ultrasonic image signal, it is necessary to transmit an ultrasonic image with a resolution level higher than the resolution information received at the resolution information reception portion 130.

Meanwhile, scan data capable of corresponding to the resolution information of the wireless communication terminal with various resolution levels and increasing efficiency of a bandwidth while wireless communication is performed may be set and mapped in advance and stored in the scan data resolution DB 140.

Following Table 2 shows a bandwidth (Mbits/sec) used according to a volume of scan data transmitted through wireless communication.

TABLE 2

| Volume of scan data | Bandwidth (Mbits/sec) |
|---|---|
| 4K BYTE | 120 |
| 2K BYTE | 60 |
| 1K BYTE | 30 |

As shown in Table 2, an occupied transmission bandwidth may vary according to the volume of the scan data.

Here, it is indicated that when the volume of the scan data is 4K bytes, pixel information of an ultrasonic image transmitted from an ultrasonic diagnostic apparatus to a wireless communication terminal through wireless communication is about 4,000 pieces.

For example, it may be known that since iPhone 4 with resolution of 640×960 in Table 1 has just scan data of 1K bytes, when the scan data of 4K bytes is transmitted, pixel information of about 3000 pieces is not used and abandoned. Here, referring to Table 2 for a transmission bandwidth, transmission bandwidths are occupied more than necessary, thereby reducing efficiency.

Accordingly, like the embodiment of the present invention, when the scan data resolution DB 140 in which scan data is set and mapped in advance is used, it is possible to efficiently utilize the transmission bandwidth.

Following Table 3 shows a scan and mapped embodiment in the scan data resolution DB 140.

TABLE 3

| Volume of scan data | Supported Resolution | | |
|---|---|---|---|
| 4K BYTE | 1200 × 1920 | 1080 × 1920 | 1536 × 2048 |
| 2K BYTE | 800 × 1280 | 720 × 1280 | 768 × 1024 |
| 1K BYTE | 480 × 800 | 640 × 960 | 640 × 1136 |

The scan data generation portion 150 may compare mapping information of the scan data resolution DB 140 and generate scan data to be transmitted to the wireless communication terminal from the frame data using the resolution information received at the resolution information reception portion 130 from the wireless communication terminal 200 according to the embodiment of Table 3.

That is, as described above, in the case of iPhone 4 with resolution of 640×960, the scan data generation portion 150 may generate scan data of 1K which supports it.

Figure 4:
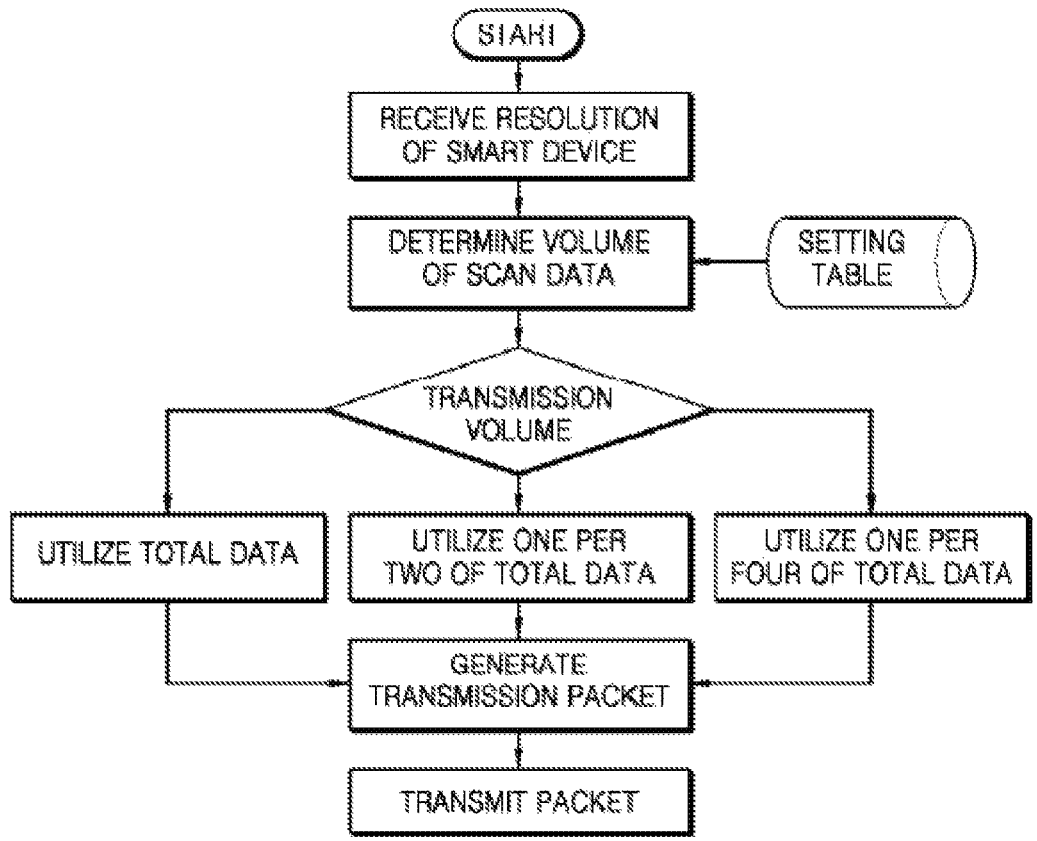
FIG. 4 is a flowchart illustrating of a process of generating a transmission packet by sampling according to a transmission volume as an embodiment.

FIG. 4 is a flowchart illustrating a process of generating a transmission packet by sampling according to a transmission volume as an embodiment.

As shown in the drawings, according to the embodiment of the present invention, a transmission packet may be generated and transmitted while the volume of total data is adjusted according to the volume of scan data.

As described above, the ultrasonic diagnostic apparatus 100 may transmit scan data generated by the scan data generation portion 150 using the scan data transmission portion 160 shown in FIG. 3.

Also, the wireless communication terminal 200 of the ultrasonic diagnostic system applicable to a wireless communication terminal with various resolution levels according to the embodiment of the present invention includes a display portion 210, a resolution information generation portion 220, a data transmission/reception portion 230, a scan-conversion resolution database 240, an application control portion 250, and a scan-conversion portion 260.

In more detail, the display portion 210 may include a display screen with various resolution levels as described above to display an ultrasonic image according to a type of a wireless communication terminal and may be provided at one of wireless communication terminals such as a personal computer (PC), a smart phone, a tablet type device, a pad type device, personal digital assistants (PDA), etc. connected through wireless communication.

The resolution information generation portion 220 may generate resolution information corresponding to the display screen of the display portion 210.

In the embodiment of the present invention, physical resolution information of the display screen may be obtained using a device driver of the display portion 210.

Here, including the resolution information generation portion 220, the scan-conversion resolution DB 240 and the application control portion 250 which will be described below may be embodied as independent application programs installed in a wireless communication terminal.

Also, the data transmission/reception portion 230 may perform wireless communication with the ultrasonic diagnostic apparatus 100 and transmit and receive the resolution information generated by the resolution information generation portion 220 of the wireless communication terminal and the scan data of the ultrasonic diagnostic apparatus 100.

Figure 5:
FIG. 5 is a view illustrating a packet structure when a data transmission/reception portion 230 transmits resolution information.

FIG. 5 is a view illustrating a packet structure when a data transmission/reception portion 230 transmits resolution information.

A packet header may indicate a packet for data communication and may store a total volume of the packet. A command may indicate an operation command to be performed using the packet or a response for the command. A body may store data corresponding to the command or the response.

Meanwhile, the scan-conversion resolution DB 240 shown in FIG. 3 may store a size of an ultrasonic image capable of being scan-converted corresponding to the resolution information generated by the resolution information generation portion 220 of FIG. 3 which is set and mapped in advance.

Following Table 4 shows a set and mapped embodiment in the scan-conversion resolution DB 240.

TABLE 4

| Volume of scan data | Supported Resolution of Wireless communication terminal | | |
|---|---|---|---|
| 1080 × 1080 | 1200 × 1920 | 1080 × 1920 | 1536 × 2048 |
| 720 × 720 | 800 × 1280 | 720 × 1280 | 768 × 1024 |
| 640 × 640 | 480 × 800 | 640 × 960 | 640 × 1136 |

As shown in Table 4, it may be known that sizes of ultrasonic images vary according to supported resolution levels of wireless communication terminals.

Accordingly, the application control portion 250 of the wireless communication terminal 200 may map an ultrasonic image corresponding to resolution information of the display screen of the display portion 210 using the scan-conversion resolution DB 240.

Next, the scan-conversion portion 260 may form an ultrasonic image adequate for resolution supported by the display screen by performing scan conversion on the scan data received from the ultrasonic diagnostic apparatus 100 using mapping information obtained from the application control portion 250.

As described above, the ultrasonic diagnostic system applicable to a wireless communication terminal with various resolution levels according to the embodiment of the present invention may increase efficiency of a transmission/reception bandwidth because the ultrasonic diagnostic apparatus 100 forms and transmits frame data obtained from the ultrasonic probe 110 as scan data corresponding to the resolution of the wireless communication terminal 200 and may be applied to the wireless communication terminal 200 with various resolution levels because the wireless communication terminal 200 may scan-convert the scan data received from the ultrasonic diagnostic apparatus 100 into an ultrasonic image adequate for the display screen with various resolution levels.

Figure 6:
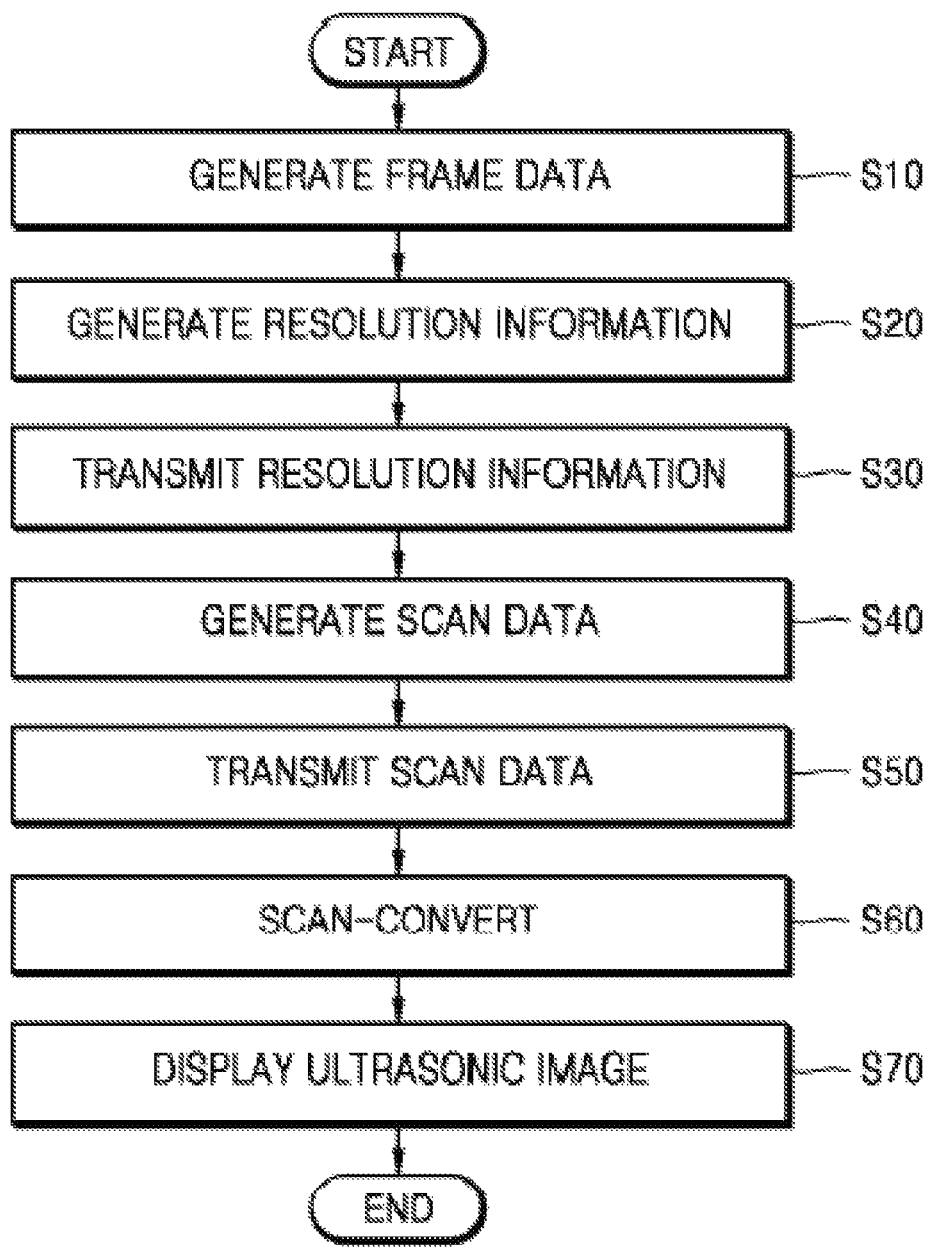
FIG. 6 is a flowchart of an ultrasonic diagnostic method applicable to a wireless communication terminal with various resolution levels according to an embodiment of the present invention.

FIG. 6 is a flowchart of an ultrasonic diagnostic method applicable to a wireless communication terminal with various resolution levels according to an embodiment of the present invention.

Referring to FIG. 6, a diagnostic method of the ultrasonic diagnostic system described with reference to FIG. 3 will be described as follows.

As shown in the drawing, the diagnostic method of the ultrasonic diagnostic system applicable to a wireless communication terminal with various levels according to the embodiment of the present invention includes generating frame data (S10), generating resolution information (S20), transmitting the resolution information (S30), generating scan data (S40), transmitting the scan data (S50), scan-converting the scan data into an ultrasonic image (S60), and displaying the ultrasonic image on a display screen (S70).

In more detail, the generating of the frame data (S10) is a first operation in which the beam former 120 which forms the ultrasonic diagnostic apparatus 100 of FIG. 3 generates the frame data using an echo signal collected by the ultrasonic probe 110.

Next, the generating of the resolution information (S20) may be an operation of performing one function of an application program independently executed by the wireless communication terminal 200 of FIG. 3.

That is, the generating of the resolution information (S20) is a second operation in which the resolution information generation portion 220 of FIG. 3 requests display information from an exclusive operating system of the wireless communication terminal 200, a resolution level of the display screen is obtained through a device driver of the operating system, and then the resolution information is generated by providing the resolution level to the application program again.

Next, the transmitting of the resolution information (S30) is a third operation in which the resolution information obtained in the second operation using the data transmission/reception portion 230 of FIG. 3 which forms the wireless communication terminal 200 and the resolution information reception portion 130 of FIG. 3 which forms the ultrasonic diagnostic apparatus 100 is transmitted from the wireless communication terminal 200 to the ultrasonic diagnostic apparatus 100.

Also, the generating of the scan data (S40) is a fourth operation in which the resolution information of the wireless communication terminal 200 obtained in the second operation is compared with mapping information of the scan data resolution DB 140 of FIG. 3 and the frame data generated by the beam former 120 of FIG. 3 is generated as scan data to be transmitted to the wireless communication terminal 200 according to the mapping information.

After that, the transmitting of the scan data (S50) is a fifth operation in which the scan data is transmitted from the ultrasonic diagnostic apparatus 100 to the wireless communication terminal 200 through the scan data transmission portion 160 of the ultrasonic diagnostic apparatus 100 of FIG. 3 and the data transmission/reception portion 230 of the wireless communication terminal 200.

Meanwhile, in the embodiment of the present invention, as a wireless communication method performed between the ultrasonic diagnostic apparatus 100 and the wireless communication terminal 200 in the third operation (S30) and the fifth operation (S50), one of Bluetooth, a wireless universal serial bus (USB), a wireless local area network (LAN), wireless fidelity (WiFi), Zigbee, and an infrared data association (IrDA).

Also, the scan-converting of the scan data into the ultrasonic image (S60) is a sixth operation in which the ultrasonic image corresponding to the resolution information is mapped by the application control portion 250 which forms the wireless communication terminal 200 referring to the scan-conversion resolution DB 240 and then the scan data received from the ultrasonic diagnostic apparatus 100 is scan-converted into an ultrasonic image adequate for resolution information of the display screen by the scan-conversion portion 260.

Next, the ultrasonic image on which scan-conversion is completed may be displayed by the display portion 210.

Hereinafter, an example of an ultrasonic diagnostic apparatus according to one embodiment of the present invention will be described.

The ultrasonic diagnostic apparatus according to one embodiment of the present invention performs receiving resolution information of a terminal wirelessly connected and operating while interconnected with the ultrasonic diagnostic apparatus from the terminal, determining scan data generated using the resolution information received from the terminal into a volume adequate for the resolution information using a setting table and a method of sampling or interpolation, and generating transmission data or a packet with respect to the ultrasonic image according to the determination and transmitting it to the terminal.

Hereinafter, an example of a terminal interconnected with the ultrasonic diagnostic apparatus according to one embodiment of the present invention will be described.

There are operations of requesting resolution information with respect to the terminal from the ultrasonic diagnostic apparatus; transmitting the resolution information of the terminal to the ultrasonic diagnostic apparatus according to the request; receiving ultrasonic image data from the ultrasonic diagnostic apparatus; and generating an ultrasonic image from the received ultrasonic image data using an image processor.

As described above, according to the embodiments of the present invention, since frame data formed by a beam former of an ultrasonic diagnostic apparatus is formed as scan data corresponding to a resolution level of a wireless communication terminal and then transmitted to the wireless communication terminal, a transmission/reception bandwidth may be efficiently utilized.

Also, since the scan data transmitted from the ultrasonic diagnostic apparatus may be independently scan-converted into an adequate resolution level at the wireless communication terminal, there are provided an ultrasonic diagnostic system and method applicable to wireless communication terminals with various resolution levels.

While the present invention has been described in detail, it should be known that the embodiments described above are only exemplary and not limitative and it will be understood that various changes in form and details may be made therein without departing from the spirit and scope of the present invention as defined by the following claims.

What is claimed is:

1. An ultrasonic diagnostic system formed of an ultrasonic diagnostic apparatus and a wireless communication terminal and applicable to multiple wireless communication terminals, each with a different resolution level, comprising:
   the ultrasonic diagnostic apparatus which:
      receives resolution information from the wireless communication terminal indicative of a resolution level of a display screen of the wireless communication terminal;
      accesses a scan data resolution database (DB) which includes a mapping of a plurality of resolution levels to corresponding scan data volume sizes;
      determines a scan data volume size that corresponds with the resolution level of the display screen of the wireless communication terminal based on the received resolution information and the mapping; and
      converts frame data obtained by collecting an echo signal at an ultrasonic probe into scan data of the determined volume size corresponding to the resolution level of the display screen of the wireless communication terminal; and
   the wireless communication terminal which receives the scan data from the ultrasonic diagnostic apparatus and scan-converts the scan data into an ultrasonic image corresponding to the resolution level of the display screen thereof.

2. The ultrasonic diagnostic system of claim 1, wherein the ultrasonic diagnostic apparatus comprises:
   an ultrasonic probe which transmits an ultrasonic signal to an object and receives an echo signal reflected by the object;
   a beam former which generates frame data by collecting the echo signal reflected from the ultrasonic probe;
   a resolution information reception portion which receives the resolution information from the wireless communication terminal;
   the scan data resolution DB;
   a scan data generation portion which compares the resolution information received by the resolution information reception portion with the mapping information of the scan data resolution DB and generates scan data to be transmitted to the wireless communication terminal using the frame data; and a scan data transmission portion which transmits the scan data generated by the scan data generation portion to the wireless communication terminal.

3. The ultrasonic diagnostic system according to claim 2, wherein the wireless communication terminal comprises:

a display portion which displays an ultrasonic image;

a resolution information generation portion which generates resolution information corresponding to a resolution level of a display screen of the display portion;

a data transmission/reception portion which transmits and receives the resolution information and receives scan data by performing wireless communication with the ultrasonic diagnostic apparatus;

a scan-conversion resolution DB which includes a mapping of a size of an ultrasonic image capable of being scan-converted from the scan data to multiple resolution levels, including the resolution level of the display screen of the display portion, which is set and mapped in advance;

an application control portion which maps an ultrasonic image corresponding to the resolution level of the display screen using the scan-conversion resolution DB; and a scan-conversion portion which scan-converts the scan data received from the ultrasonic diagnostic apparatus into an ultrasonic image corresponding to the resolution level of the display screen.

4. The ultrasonic diagnostic system according to claim 1, wherein the wireless communication terminal comprises:

a display portion which displays an ultrasonic image;

a resolution information generation portion which generates resolution information corresponding to a resolution level of a display screen of the display portion;

a data transmission/reception portion which transmits the resolution information and receives scan data by performing wireless communication with the ultrasonic diagnostic apparatus;

a scan-conversion resolution DB which includes a mapping of a size of an ultrasonic image capable of being scan-converted from the scan data to multiple resolution levels, including the resolution level of the display screen of the display portion, which is set and mapped in advance;

an application control portion which maps an ultrasonic image corresponding to the resolution level of the display screen using the scan-conversion resolution DB; and a scan-conversion portion which scan-converts the scan data received from the ultrasonic diagnostic apparatus into an ultrasonic image corresponding to the resolution level of the display screen.

5. A diagnostic method of an ultrasonic diagnostic system applicable to a wireless communication terminal and comprising an ultrasonic diagnostic apparatus which forms scan data corresponding to a resolution level of a display screen of the wireless communication terminal using frame data obtained by collecting an echo signal from an ultrasonic probe and the wireless communication terminal which receives the scan data from the ultrasonic diagnostic apparatus and scan-convert the scan data into an ultrasonic image corresponding to the resolution level of the display screen, the method comprising:

a first operation of generating the frame data, by a beam former, by collecting the echo signal of the ultrasonic probe;

a second operation of generating resolution information of the display screen, by a resolution generation portion of the wireless communication terminal, using a device driver;

a third operation of transmitting the resolution information from the wireless communication terminal to the ultrasonic diagnostic apparatus through a data transmission/reception portion of the wireless communication terminal and a resolution information reception portion of the ultrasonic diagnostic apparatus;

a fourth operation of comparing the resolution information of the wireless communication terminal with mapping information of a scan data resolution DB of the ultrasonic diagnostic apparatus, the mapping information including a mapping of a plurality of resolution levels to corresponding scan data volume sizes, and then generating scan data to be transmitted to the wireless communication terminal using the frame data generated by the beam former according to the mapping information;

a fifth operation of transmitting the scan data from the ultrasonic diagnostic apparatus to the wireless communication terminal through a scan data transmission portion of the ultrasonic diagnostic apparatus and the data transmission/reception of the wireless communication terminal;

a sixth operation of mapping an ultrasonic image corresponding to the resolution information, by an application control portion, by referring to a scan-conversion resolution DB and then scan-converting the scan data received from the ultrasonic diagnostic apparatus, by a scan-conversion portion, into an ultrasonic image corresponding to the resolution information of the display screen; and a seventh operation of displaying the ultrasonic image on which scan conversion is completed by a display portion.

* * * * *